United States Patent
Erdmann et al.

(10) Patent No.: US 10,548,616 B2
(45) Date of Patent: Feb. 4, 2020

(54) TOURNIQUET CUFF

(71) Applicant: ulrich GmbH & Co. KG, Ulm (DE)

(72) Inventors: Sven Erdmann, Ulm (DE); Uwe Striggow, Aichtal (DE); Sarah Andrea Diana Wimböck, Ulm (DE)

(73) Assignee: ulrich GmbH & Co. KG, Ulm (DE)

( * ) Notice: Subject to any disclaimer, the term of this patent is extended or adjusted under 35 U.S.C. 154(b) by 294 days.

(21) Appl. No.: 15/673,871

(22) Filed: Aug. 10, 2017

(65) Prior Publication Data

US 2018/0042614 A1 Feb. 15, 2018

(30) Foreign Application Priority Data

Aug. 12, 2016 (DE) .................. 10 2016 115 027

(51) Int. Cl.
*A61B 17/00* (2006.01)
*A61B 17/132* (2006.01)
*A61B 17/135* (2006.01)

(52) U.S. Cl.
CPC .. *A61B 17/135* (2013.01); *A61B 2017/00526* (2013.01); *A61B 2017/00862* (2013.01); *A61B 2017/00955* (2013.01)

(58) Field of Classification Search
CPC ... A61B 17/135; A61B 17/1355; A61B 17/12; A61B 2017/00526; A61B 2017/00831; A61B 2017/00862; A61B 17/00; A61B 17/132; A61B 5/30; A61B 5/02233
See application file for complete search history.

(56) References Cited

U.S. PATENT DOCUMENTS

| | | | |
|---|---|---|---|
| 2,045,750 A | 6/1936 | Buschenfeldt | |
| 2,291,785 A | 8/1942 | Baudistel | |
| 3,633,567 A * | 1/1972 | Sarnoff | A61B 5/02141 600/499 |
| 4,637,394 A | 1/1987 | Racz et al. | |
| 2012/0116444 A1* | 5/2012 | Zodnik | A61B 17/12 606/202 |
| 2013/0289612 A1 | 10/2013 | McEwen et al. | |

FOREIGN PATENT DOCUMENTS

DE 3333311 A1 4/1985

OTHER PUBLICATIONS

Result of examination report for German Patent Application No. 10 2016 115 027.4 filed Aug. 12, 2016.

* cited by examiner

*Primary Examiner* — Vi X Nguyen
(74) *Attorney, Agent, or Firm* — Paul D. Bianco; Gary S. Winer; Fleit Intellectual Property Law (57) ABSTRACT

A tourniquet cuff for placement on a limb, having an inflatable body which encloses an inflatable chamber and which can be inflated with a compressed gas so as to create blood flow restriction in the limb, with the inflatable body being formed from an elongated support made of a bendable support material extending along a longitudinal direction and from a stretchable wall made of a stretchable material attached to the support. To enable thorough and easy cleaning and sterilization of the tourniquet cuff and easy placement on a limb and to ensure the most uniform possible distribution of the pressure exerted by the tourniquet cuff on the limb, the stretchable wall is affixed to the elongated support while the stretchable material is stretched at least in the longitudinal direction. A method of manufacturing the tourniquet cuff is also disclosed.

18 Claims, 4 Drawing Sheets

TOURNIQUET CUFF

FIELD OF THE DISCLOSURE

The disclosure relates to a tourniquet cuff for placement on a limb and for creating blood flow restriction in the limb as well as to a method of manufacturing such a tourniquet cuff.

BACKGROUND

Blood flow restriction devices in the form of inflatable cuffs are known from the prior art, e.g., from U.S. Pat. No. 4,637,394 B, which cuffs can be placed on a limb and be inflated in order to create blood flow restriction in the limb. To create blood flow restriction in the limb, the inflatable cuff is connected to a compressed gas source and inflated with compressed gas (for example, compressed air) to such an extent that the cuff exerts a sufficiently high pressure on the limb so as to interrupt, at least to a large extent or completely, the flow of blood through the part of the limb that is enclosed by the cuff. Such blood flow restriction devices are used, for example, in surgical interventions on limbs, in which extensive or complete blood flow restriction or even a bloodless field in the area of operation must be created and maintained during surgery in order to make the surgical procedure easier or to reduce the risk of injury to the vascular system. To inflate the cuff, the cuff is connected to a variable compressed gas source via a hose, by means of which the cuff can be inflated with a variable predefined pressure. The compressed gas source is controlled by a control device, by means of which an operator can control the inflation of the cuff as well as the release of pressure when the blood flow restriction is to be stopped.

Because of the extremely variable and individual sizes and shapes of the limbs of patients, a hospital, as a rule, must keep in stock a multiplicity of tourniquet cuffs in different sizes and shapes. This is labor-intensive and expensive. To solve this problem, U.S. 2013/028 96 12 A1 proposes an inexpensive tourniquet cuff for one-time use, which can be used on different non-cylindrical limbs. This tourniquet cuff comprises a substantially arcuate outer wrap which contains an inflatable bag. Disposed on the outside surface of the wrap is a fastening belt made of an unstretchable material. Using this fastening belt, the cuff, the end sections of which are looped about the limb so as to overlap, is attached to the limb. The wrap is made of a textile material, in particular a knitted or woven nylon fabric, which is sterilized before the cuff is attached to a limb. Because of the flexible textile structure of the wrap of the cuff, there is the risk of creases forming in the wrap. Creases can form especially while the cuff is being inflated since the inside circumference becomes shorter than the outside circumference, thereby creating excess material which leads to the formation of creases. In addition, the prior-art tourniquet cuff disclosed in U.S. 2013/028 96 12 A1 cannot be adequately cleaned and sterilized and is intended for one-time use only, which, with respect to the generation of waste and from the standpoint of resource efficiency, is a considerable drawback.

Furthermore, it has also been demonstrated that when using the prior-art tourniquet cuffs which comprise a wrap made of a textile fabric or rubber and which are looped about the limb so as to at least partially overlap, the pressure exerted by the cuff on the underlying limb is not distributed uniformly. This non-uniform pressure distribution is attributable, on the one hand, to the irregular shape of the limb, which, as a rule, does not have a uniformly cylindrical shape and, on the other hand, to the creases that form in the textile fabric or in the rubber material during placement and inflation of the cuff. To ensure that the pressure exerted on the limb is as uniform as possible, the cuff must be wrapped around the limb so as to be absolutely flat and creaseless. Creases and overlaps produce pressure points which can later manifest themselves as tension blisters or skin necroses.

A surgical cuff for attachment to a limb is known from U.S. Pat. No. 2,291,785 B. This cuff comprises a truncated cone-like and tubular main body which has an inside and an outside wall made of a thin, flexible and stretchable material, with the two walls being connected to each other along their outside ends and with the remaining wall area extending at a distance from each other. On one end, the two walls are connected to each other, thereby forming an external annular portion which is flexible and stretchable both in the longitudinal and in the transverse direction. Disposed between the two walls are a plurality of layers made of a woven fabric, which layers are connected to each other and to the two walls by means of a rubber adhesive. On the other end that lies opposite to the external annular portion, the walls are reinforced with textile strips, so that the main body, although flexible and bendable as a whole, is stretchable only in the area of the annular portion. Located opposite to the inside wall and radially disposed on its inside surface is a lining wall made of a flexible and stretchable rubber material, the edge portions of which lining wall are connected to the two walls so that a sealed annular chamber is formed between the inside wall of the main body and the lining wall, which chamber can be inflated by means of compressed air. When unpressurized and uninflated, the lining wall and the oppositely lying inside wall extend coaxially relative to each other. Because of the stiffness of the main body, essentially only the lining wall expands radially inwardly when compressed air is blown into the chamber. Along four diametrically oppositely lying areas, the lining wall is attached in the longitudinal direction to the inside wall, thereby causing indentations to be formed in these areas, which have a higher resistance to the stretching of the lining wall, with the result that during inflation, between these indentations, radially inwardly projecting bulges form which extend in the longitudinal direction. The uninflated (unpressurized) main body is placed on a limb and is subsequently inflated, during the course of which the radially inwardly swelling bulges exert pressure on the limb. The advantage of this design is that pressure is not exerted over the entire circumferential area of the main body, but only on the area of the bulges, so that this pressure allows the flow of arterial blood in the limb but largely interrupts the flow of venous blood. However, tourniquet cuffs require that the pressure exerted on the limb be uniform across the entire circumference so as to arrest the flow of blood and to create blood flow restriction.

As the foregoing shows, there is a need for an improved tourniquet cuff for placement on a limb, which cuff can be thoroughly and easily cleaned and sterilized, easily and quickly applied to the limb and able reliably to create a long-lasting blood flow restriction in the limb, while at the same time ensuring that the pressure exerted by the tourniquet cuff on the limb is distributed as uniformly as possible and that stresses on the tissue and the skin of the limb are minimized as much as possible.

SUMMARY

A tourniquet cuff and a method of manufacturing a tourniquet cuff are disclosed herein.

The tourniquet cuff according to the present disclosure is intended for placement on a limb and comprises an inflatable body, which can be inflated by means of a compressed gas, which inflatable body encloses an inflatable chamber and is formed by an elongated support made of a bendable support material and extending in a longitudinal direction and by a stretchable wall made of a stretchable material, which wall is affixed to the support. While the stretchable material is stretched at least in the longitudinal direction, the stretchable wall is affixed to the elongated support, which is made of a bendable, but non-elastic support material. Due to the stretching of the stretchable wall and the lesser stretchability of the support material compared with the stretchable material, on the one hand, the stretchable wall, at least in the longitudinal direction, exerts a tensile stress on the elongated support, which has the effect that the support is deformed into an annular shape, and, on the other hand, the stretchable wall, even when the inflatable body is not pressurized, curves into a convex shape. Due to the annular deformation of the support and the convex curvature of the stretchable wall, the overall resulting shape, even when the inflatable body is not pressurized, is that of a torus (which is interrupted along the transverse edges of the support and which radially has an annular shape on the outside), with the inflatable body, even when not pressurized (i.e., at ambient pressure in the inflatable body), being dimensionally stable and free of creases.

Both the support material and the stretchable material are gas-tight and, more specifically, air-tight. The inflatable body suitably has two oppositely lying ends with transverse edges and with longitudinal edges extending in the longitudinal direction in between, with the stretchable wall, along its circumferential edges, being air-tightly connected, in particular glued or heat-sealed, to the support, thereby forming a gas-tight (air-tight) inflatable chamber between the support and the stretchable wall. This chamber suitably has an opening, to which a gas hose (compressed air hose) for the delivery of a compressed gas (compressed air) can be connected. The opening is suitably disposed in the area of a longitudinal edge or a transverse edge of the inflatable body, thereby ensuring that a hose connected to the opening does not pose an obstruction when the cuff is being closed (for example, by means of Velcro fasteners which are attached to the outside circumference of the cuff).

The tourniquet cuff is applied to a limb to create blood flow restriction by looping the cuff around the limb and by placing the (transverse) ends of the unpressurized inflatable body one on top of the other so that they overlap and by affixing them to each other, for example, by means of adhesive or Velcro fasteners. Thus, when a tourniquet cuff has been applied to a limb, the inflatable body is toroidally looped around the limb, with the stretchable wall facing and lying close to the limb, while slight pressure is being exerted by the fastening means. During the course of this, the stretchable wall, which, when not inflated, is convexly curved (facing away from the support), is compressed by the pressure exerted by the fastening means until it rests partially or fully on the inside surface of the support. At the same time, the air still contained in the unpressurized (i.e., at ambient pressure) inflatable body is pushed out of the opening and the potentially connected hose. Due to the elasticity of the stretchable material, no creases form in the stretchable material.

During inflation of the inflatable body with a compressed gas (particularly, compressed air), the stretchable wall curves radially inwardly in the direction of the limb and thereby exerts pressure on the limb. By controlling the pressure generated by the compressed gas source, the pressure exerted by the tourniquet cuff on the limb can be adjusted so that it is markedly higher than the arterial systolic blood pressure of the patient, thereby creating blood flow restriction in the limb. In patients with normal blood pressure (RR≤150 mmHg), an effective blood flow restriction is obtained when the pressure exerted on the limb is approximately 250 mmHg on the arm and approximately 350 mmHg or above on the leg.

When the cuff is in place, the support is positioned radially on the outside and, because of its lesser stretchability or elasticity compared with the stretchable wall, prevents the inflatable body during inflation from appreciably curving radially outwardly. As a result, the pressure of the compressed gas necessary to create blood flow restriction can be kept lower, thereby saving energy for maintaining the compressed gas at a high pressure.

To prevent the inflatable body from appreciably curving radially outwardly, it is recommended that the ratio of the modulus of elasticity of the support material to the modulus of elasticity of the stretchable material be higher than 10, and preferably higher than 100.

The stretchable materials used are preferably elastomeric polymers, in particular thermoplastic elastomers (TPE) or terpolymeric elastomers, in particular rubber, ethylene propylene diene monomer (EPDM) rubber or ethylene propylene monomer (EPM) rubber, rubber materials or silicones and silicone rubber. However, the stretchable materials used can also be stretchable woven or knitted fabrics that are coated with an air-tight and stretchable material. An advantage can be obtained if the stretchable material has a Shore hardness in a range of 17 to 100 Shore A and/or a modulus of elasticity in a range of 0.05 to 10 MPa.

The support is preferably formed from a flat plastic plate, especially one made of a thermoplastic material, such as polycarbonate (PC), polyethylene terephthalate (PET), polyethylene (PE), polypropylene (PP), polystyrene (PS), polyether ether ketone (PEEK), polyvinylidene fluoride (PVDF) and polyvinyl chloride (PVC), or from a metal sheet. An advantage can be obtained if the support is made of a sterilizable support material so as to make it possible to sterilize and thus to use the tourniquet cuff repeatedly.

Thus, the tourniquet cuff according to the present disclosure comprises an inflatable body having a first portion in the form of the stretchable wall made of an elastically stretchable material (stretchable material) and a second portion disposed radially on the outside in the form of the support which is configured to be more rigid than the stretchable first portion, thereby ensuring that during inflation, the inflatable body can at least for the most part curve radially inwardly in the direction of the limb to which the tourniquet cuff is attached, but not, or at least only slightly, radially outwardly. To this end, in contrast to the stretchable first portion disposed radially on the inside, the second portion disposed radially on the outside is made of a stiffer (i.e., less stretchable) material which, during inflation of the inflatable body, is deformed (stretched) to a lesser degree than the first portion (stretchable wall). During inflation of the inflatable body, this portion therefore stretches only radially inwardly and thereby exerts pressure on the limb which, relative to the inflatable body, is disposed radially on the inside. At the same time, the stretchable wall, which forms the first radially inside portion of the inflatable body, curves convexly in the direction of the limb. During inflation of the inflatable body, the convex curvature ensures a uniform distribution of the pressure on the limb. Because of the convex shape, the inflatable body during inflation adjusts optimally to the shape of the limb. Due to the elasticity of the stretchable material of the stretchable wall in its first portion facing the limb, the blood flow restriction device can also be used on limbs having variable circumferences and/or a non-cylindrical shape (i.e., for example, having a substantially conical shape) or can be applied to different parts of a limb with variable circumferences and to different limbs having a non-cylindrical shape. It is therefore not necessary to keep in stock a multiplicity of tourniquet cuffs of varying sizes and shapes for different limbs or patients since the tourniquet cuff according to the present disclosure can be used at least for the standard cases.

Due to the fact that the stretchable wall is pre-tensioned on the support, the inflatable body of the tourniquet cuff according to the present disclosure is dimensionally stable and self-supporting even when unpressurized (i.e., when uninflated). Due to the flexible and stretchable design, on the one hand, and the dimensionally stable basic shape of the inflatable body, on the other, when uninflated, the inflatable body is free of creases and, during inflation, can expand without forming creases. Since the inflatable body, when uninflated, is free of creases, the tourniquet cuff according to the present disclosure can be prepared more simply for repeated use, for example, by cleaning with a disinfectant or by sterilization.

The basic shape of the inflatable body, which is dimensionally stable even when uninflated, furthermore ensures that, during inflation, the compressive pressure exerted on the limb is uniformly distributed over the inside circumference of the inflatable body. Due to the elasticity of the stretchable first portion of the inflatable body, the inflatable body, during inflation, conforms snugly to the shape of the limb. As a result, constrictions in the limb due to pressure in areas with a larger circumference or diameter are avoided, and slipping of the tourniquet cuff along the limb is also prevented. In addition, skin injuries to the limb are thereby prevented, and the stress on the tissue in the limb is lower throughout the blood flow restriction time.

To manufacture a tourniquet cuff according to the present disclosure, an elongated support extending along a longitudinal direction (L) and having a predefined length is used, with the support material being gas-tight, in particular air-tight, and bendable, but unstretchable or only just stretchable. Suitably, the support has the shape of a flat, rectangular strip with longitudinal edges extending in the longitudinal direction and with an inside surface and an outside surface. In addition, an elongated stretchable wall, which also extends along a longitudinal direction and which is made of a gas-tight or, more specifically, air-tight, stretchable material having a predefined length is provided and cut to size to conform to the shape and dimensions of the support, with the length of the stretchable wall being shorter than the length of the support and with the width of the stretchable wall suitably conforming to the width of the support. Suitably, the stretchable wall also has a rectangular, in particular, a strip-type, shape with circumferential edge portions which are disposed in the area of the longitudinal edges and the transverse edges. While the stretchable wall is stretched in the longitudinal direction, the stretchable wall is placed on top of the inside surface of the support in such a way that the stretchable wall is aligned with the support. The stretchable wall is stretched to such an extent that its stretched length conforms to the length of the support. Subsequently, the edge portions of the stretchable wall are attached to the support so as to be gas-tight or, more specifically, air-tight, for example, by means of gluing or heat-sealing, so that a gas-tight inflatable chamber is formed between the inside surface of the support and the stretchable wall. Due to the stretching, the stretchable wall exerts a tensile stress on the support in the longitudinal direction, which has the effect that the support material is deformed into an annular shape, on the one hand, and that the stretchable wall curves convexly (facing away from the support) outwardly. As a result, an inflatable body is formed, which essentially has the shape of a torus (with interrupted transverse edges) and which encloses an inflatable chamber, with the outside surface of the support being radially positioned on the outside and with the convexly curved stretchable wall being radially positioned on the inside.

Finally, an opening into the inflatable body can be formed, suitably in the area of a longitudinal edge of the support, and a connecting part can be disposed on the opening, via which part the inflatable body can be connected to the pressure hose so as to be able to feed compressed gas into the inflatable chamber. Instead of a connecting part, a hose section, which can be connected to a compressed gas source, can be disposed directly on the opening. A fastening means, for example, a Velcro fastener or an adhesive tape is then suitably attached to the outside surface of the support, by means of which fastening means the inflatable body can be affixed to a limb.

The inflatable chamber can be divided into a plurality of chambers which are separated from each other by chamber walls. The chamber walls are integrally molded to the inside surface of the support and, in the case of a cuff that is deformed into an annular shape, extend in the radial direction between the inside surface of the support and the stretchable wall and can, for example, be made of a stretchable and compressible plastic or rubber material. Along their radially inwardly facing outside edge, which rests against the stretchable wall and is preferably connected thereto, the chamber walls are suitably circularly rounded off and thereby conform to the convex shape of the stretchable wall. Neighboring chambers are suitably connected in a fluidically efficient manner to each other by means of passages in the chamber wall that separates the two chambers. Through these passages in the chamber walls, a compressed gas (compressed air) flowing via an outside opening into one of the chambers can be uniformly distributed in the individual chambers, thereby ensuring that the resulting pressure is uniform in all chambers.

In this embodiment, the first portion of the inflatable body, which is stretchable and formed by the stretchable wall, serves to ensure that the chambers are able to stretch within the predefined shape of the stretchable portion. In this embodiment, the convex basic shape of the stretchable wall (which it already has because the wall was pre-tensioned on the support) is supported by the chamber walls and maintained especially when not pressurized.

These and other advantages and features of the blood flow restriction device according to the present disclosure follow from the embodiment example which is described in greater detail below with reference to the accompanying drawings. The drawings show.

DETAILED DESCRIPTION

Figure 1A:
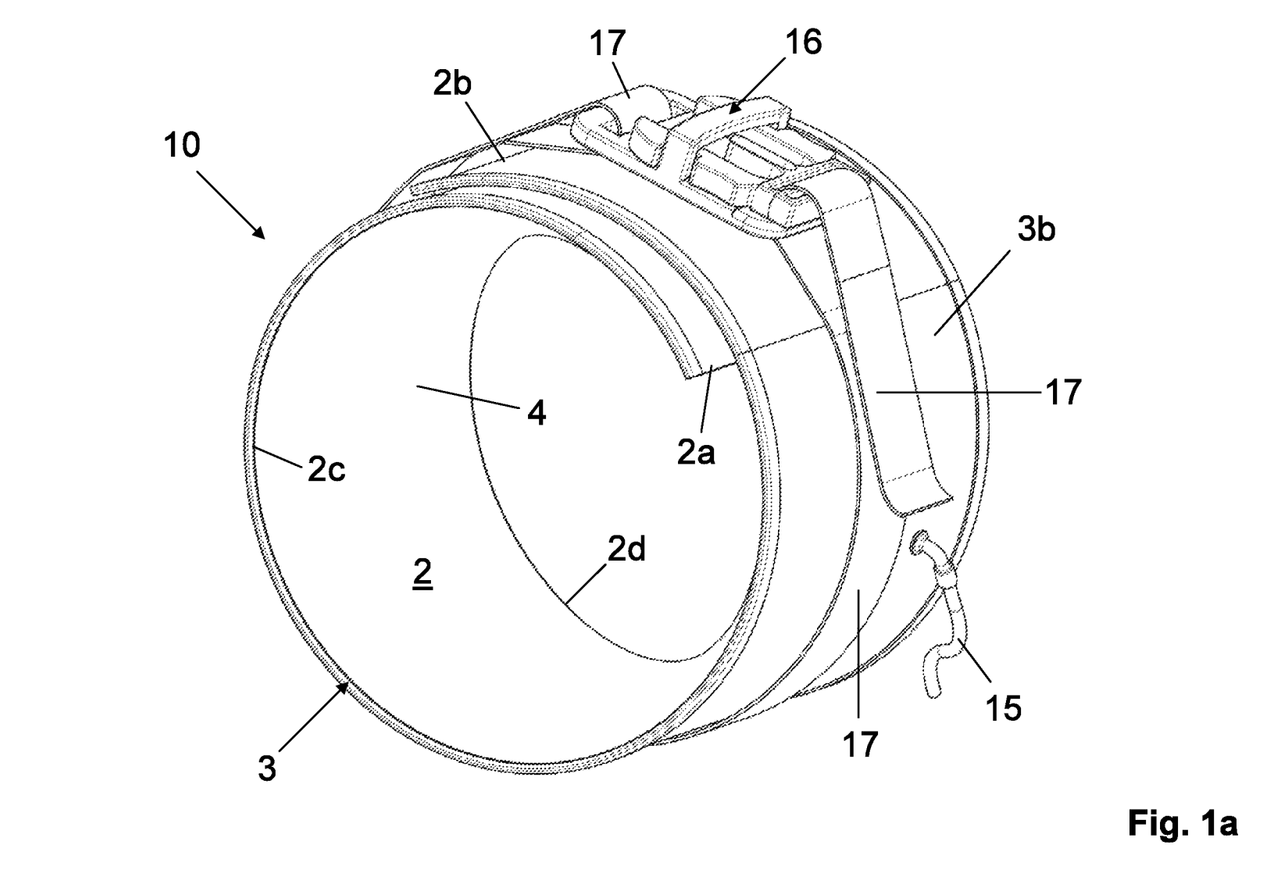
FIG. 1a: A perspective view of a tourniquet cuff according to the present disclosure.
Figure 1B:
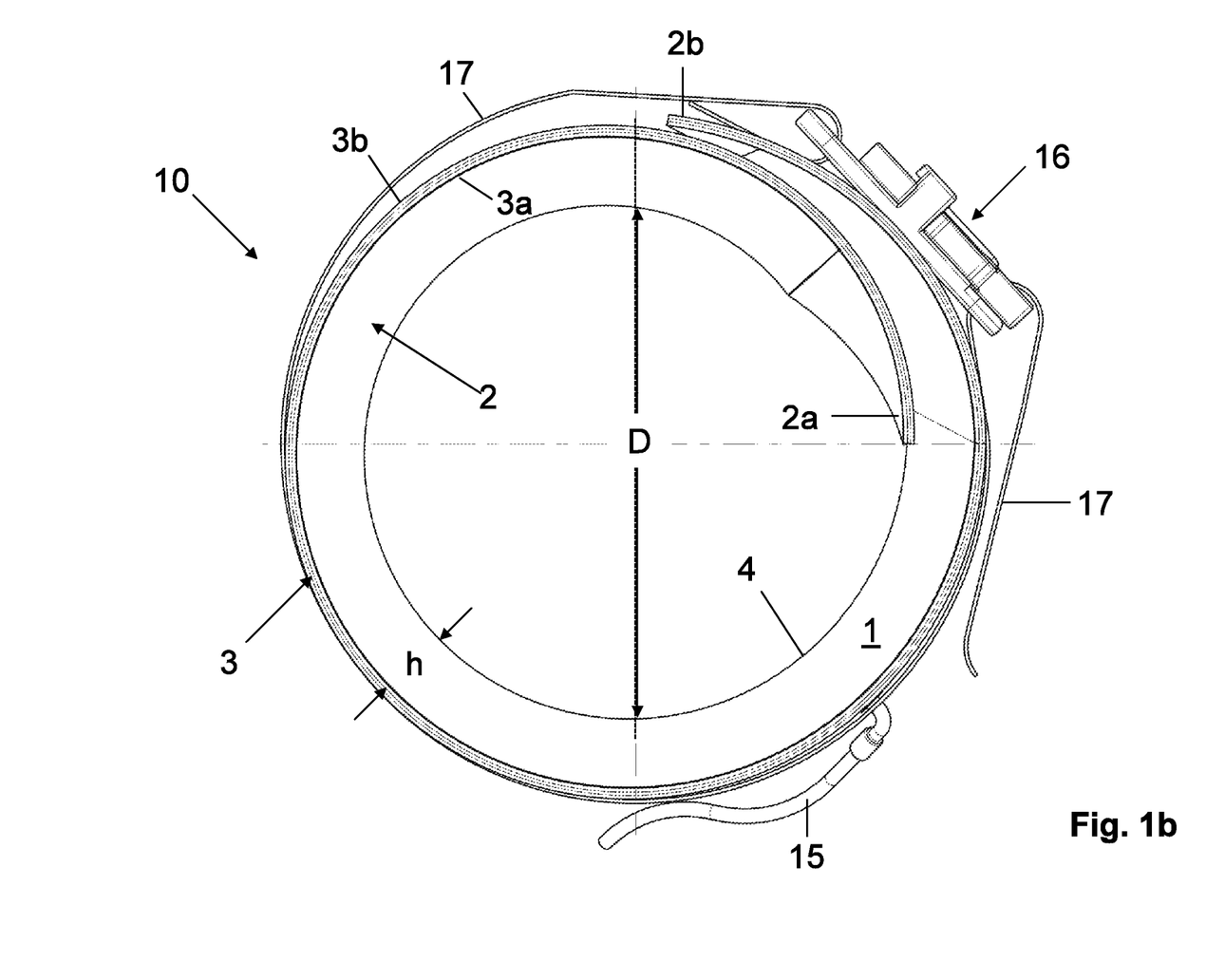
FIG. 1b: A lateral view of the tourniquet cuff according to the present disclosure seen in FIG. 1, FIG. 2a: A plan view of the tourniquet cuff seen in FIG. 1.

FIGS. 1a and 1b show a tourniquet cuff 10 according to the present disclosure for placement on a limb. The tourniquet cuff 10 comprises an inflatable body 2 which encloses an air-tight inflatable chamber 1. The inflatable body 2 can be connected via a hose 15, which is connected to the inflatable chamber 1, to a compressed gas source (not shown). The compressed gas source can, for example, be a compressor which provides compressed gas, particularly compressed air, by means of which the inflatable body can be inflated. The pressure with which the inflatable body 2 is inflated is controlled by the control unit contained in the compressed gas source. This type of control unit for controlling tourniquet cuffs is known from the prior art. Attached to the outside surface of the inflatable body 2 is a fastening tape 17 with a fastener 16. Using the fastener 16, which in this case is configured in the form of a snap fastener, the fastening tape 17 can be affixed in any position desired so as to be able to attach the tourniquet cuff 10 snugly to a limb. Instead of the fastener 16, the fastening tape can also be a Velcro tape.

Figure 2A:
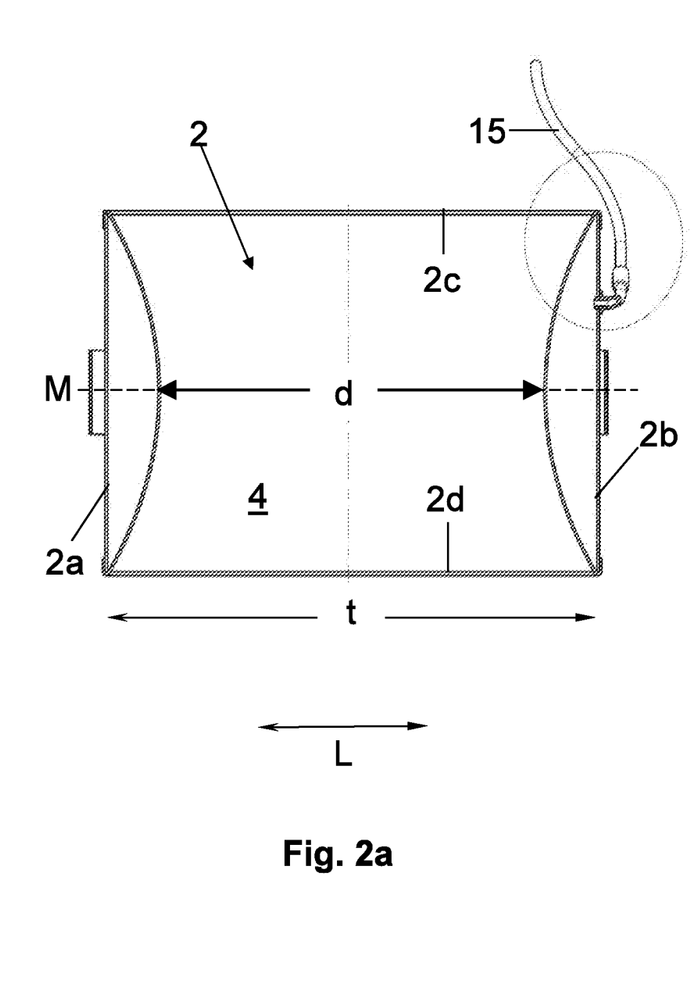
Figure 2B:
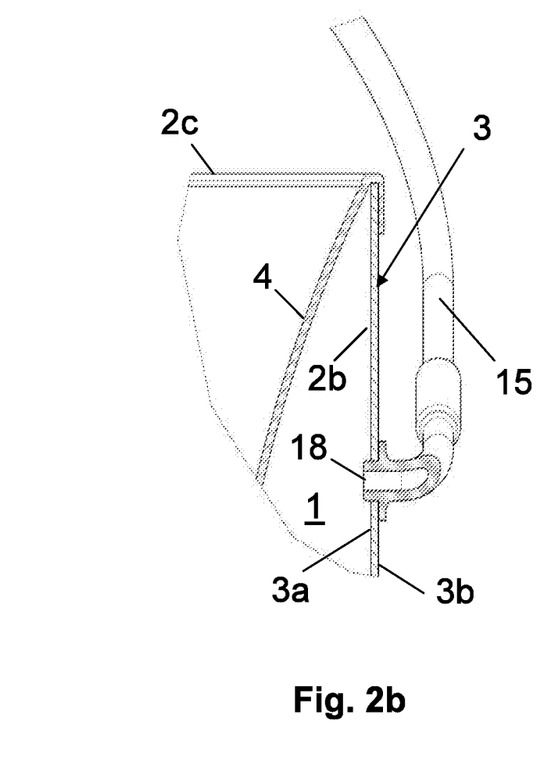
FIG. 2b: A detail view of the area of the hose, by means of which the tourniquet cuff can be connected to a compressed gas source.

FIG. 2 shows a plan view (FIG. 2a) of the tourniquet cuff 10 seen in FIG. 1 and a detail sectional view of the area of hose 15 (FIG. 2b).

As FIG. 2a indicates, the inflatable body 2 is constructed from an elongated support 3 made of a bendable support material extending in a longitudinal direction L and a stretchable wall 4 made of a stretchable material and affixed to the support 3. While stretching the stretchable material at least in the longitudinal direction, the stretchable wall 4 is affixed to the elongated support 3.

To create a gas-tight or, more specifically, an air-tight, inflatable chamber 1 between the support 3 and the stretchable wall 4, both the support material and the stretchable material are designed to be gas-tight, or more specifically air-tight, and the stretchable wall 4 is attached to, especially glued or heat-sealed to, the support 3 so as to produce a gas-tight, or more specifically, an air-tight, connection.

The support material of the support 3 used is a bendable, but at least an essentially non-elastic material, for example, a thermoplastic material, such as PE, PP or preferably polyvinylidene fluoride (PVDF), or a metal sheet. The support material is at least for the most part considerably less stretchable than the stretchable material from which the stretchable wall 4 is made.

The stretchable material of the stretchable wall 4 is an elastic (stretchable) material, for example, a rubber material or a stretchable plastic sheet. The stretchable material can also be a textile material (for example, polyester), which is coated with an air-tight coating (for example, made of polyurethane). The coating can be applied to one side or to both sides of the textile material. The stretchable material can be uniaxially or biaxially stretchable. If a biaxially-stretchable stretchable material is used, the stretchable wall 4, in addition to being attached to the support 3 so as to be stretched in the longitudinal direction L, can also be attached so as to be stretched in the transverse direction, whereas, it is preferred, however, that the stretchable wall 4 be stretched only in the longitudinal direction L.

The stretchable material is preferably stretched to an elongation of at least 250%, and stretching the stretchable material to an elongation of up to 450% is possible. Suitably, the stretchable material has a Shore hardness in a range of 17 to 100 Shore A and a modulus of elasticity in a range of 0.05 to 10 MPa. The modulus of elasticity of the stretchable material is considerably lower than the modulus of elasticity of the support material. The ratio of the modulus of elasticity of the support material to the modulus of elasticity of the stretchable material is higher than 10 and preferably higher than 100.

Due to the stretching of the stretchable wall 4 and the lesser stretchability of the support material compared with the stretchable material, the stretchable wall 4 exerts a tensile stress on the elongated support 3, at least in the longitudinal direction L (and possibly also in the transverse direction if the stretchable wall is also pre-tensioned transversely to the longitudinal direction on the support 3). This has the effect, on the one hand, that the support 3 is deformed into an annular shape, as illustrated in FIGS. 1 and 2b. On the other hand, the stretching of the stretchable wall 4 on the support 3 causes the stretchable wall 4 to curve convexly (convex curvature of the stretchable wall 4 relative to the surface of the support 3), as especially clearly seen in FIG. 2b. As a result of the annular deformation of the support 3 and the convex curvature of the stretchable wall 4, the resulting shape, even when the inflatable body is not pressurized (i.e., at ambient pressure in the inflatable chamber 1), is, as shown in the figures, that of a toroid which is interrupted along the transverse edges of the support and which, radially on the outside, has an annular shape. The inflatable body 2 is therefore dimensionally stable even when not pressurized and, due to the stretching, has no creases, especially in the area of the stretchable wall 4.

In the embodiment example of a tourniquet cuff according to the present disclosure shown in the drawings, the inflatable body has 2 two oppositely lying ends 2a, 2b with transverse edges and with longitudinal edges 2c, 2d extending in the longitudinal direction L in between (FIG. 2a). Along its edges, the stretchable wall 4 is circumferentially and air-tightly connected to the support 3, for example, by gluing or heat sealing. The stretchable wall 4 is positioned opposite to an inside surface 3a of the support 3 (FIG. 2b). The inflatable chamber 1, which, due to the air-tight structure of the support material and the stretchable material and due to the air-tight attachment of the stretchable wall 4 to the support 3, is gas-tight or, more specifically, air-tight, extends between the inside surface 3a of the support 3 and the (stretched) stretchable wall 4. In the inflatable body 2, an opening 18 is suitably disposed in the area of a longitudinal edge of the support 3, to which opening a hose 15, for example, a compressed air hose, is connected, which can be connected to a compressed gas source so as to be able to feed compressed gas, particularly, compressed air, into the inflatable chamber 1 (FIG. 2b).

Disposed on the outside surface 3b of the support 3 is a fastening means. This fastening means can be, for example, a Velcro fastening tape or an adhesive tape which can be attached to the outside surface 3b of the support through the action of Velcro or an adhesive. In the embodiment example shown in the drawings, the fastening means is an unstretchable or only sparingly stretchable fastening tape 17 with a snap fastener 16, by means of which the fastening tape can be affixed in any position desired (FIG. 1).

As the plan view of FIG. 2*a* indicates, the oppositely lying ends 2*a*, 2*b* of the inflatable body 2 overlap each other, thereby forming an overall and substantially torus-shaped inflatable body 2. The inside circumference of the toroidally bent inflatable body 2 encloses a passage with an inside diameter D, which is largest in the area of the longitudinal outside edges 2*c*, 2*d* of the inflatable body 2 and smallest in the area of the longitudinal center axis M. This path of the inside diameter of the inflatable body 2 results from the convex curvature of the stretchable wall 4 in the radial inward direction, which curvature is present even when the inflatable body 2 is unpressurized. In the area of the longitudinal center axis M of the inflatable body 2, the stretchable wall 4, which curves convexly away from the support 3, is at a (maximum) distance h from the inside surface 3*a* of the support 3, which distance is suitably in a range of 1 to 3 cm, for example, 2 cm. The exact distance h depends on the stretching properties of the stretchable materials and can be adapted to the intended use of the tourniquet cuff during production.

To create blood flow restriction in a limb, the tourniquet cuff according to the present disclosure is placed on the limb by looping the inflatable body 2 (which is bent into the shape of a toroid even when not compressed) about the limb, with the opposite ends 2*a*, 2*b* of the inflatable body 2 overlapping each other. The inflatable body 2 is affixed under tensile stress to the limb by means of the fastening means disposed on the outside surface 3*b* of the support 3. The tensile stress is suitably selected to ensure that the stretchable wall 4 is pushed far enough in the direction of the inside surface 3*a* of the support 3 so that the wall rests at least partially, preferably completely, against or on the inside surface 3*a*. The inflatable body 2 affixed in this manner to the limb is subsequently pressurized with a compressed gas, particularly, compressed air, which is fed into the inflatable chamber 1 via the hose 15. As a result of the inflow of the compressed gas into the inflatable chamber 1, the stretchable wall 4 curves radially inwardly and thereby exerts compressive pressure on the enclosed limb. The elasticity of the stretchable material and the rigidity of the support material ensure that the inflatable body 2 substantially expands only radially inwardly (but not radially outwardly). The pressure of the compressed gas flowing into the inflatable chamber 1 is controlled by means of a control device, so that blood flow restriction in the limb is created for a predefined length of time.

Figure 3A:
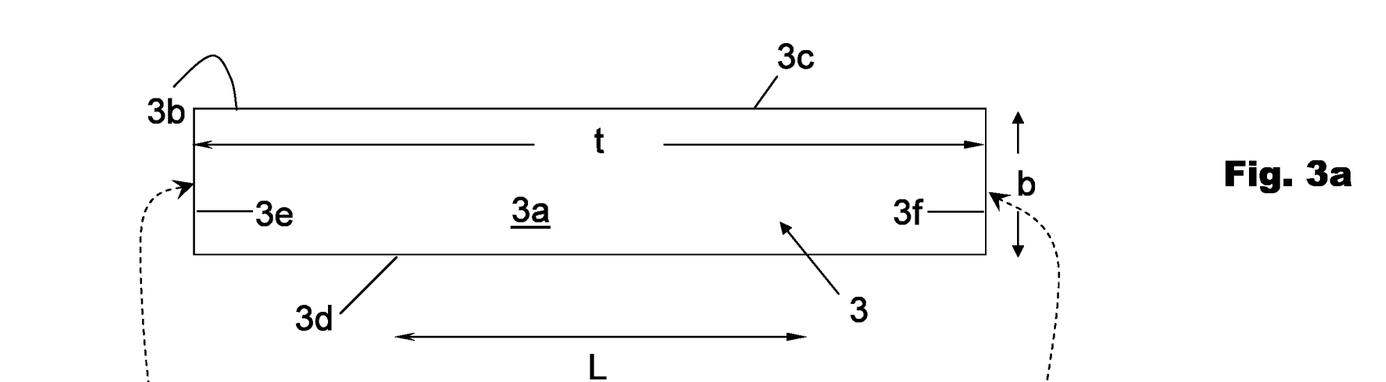
FIG. 3a: A schematic representation of the configuration and manufacture of a tourniquet cuff according to the present disclosure, showing the support.
Figure 3B:
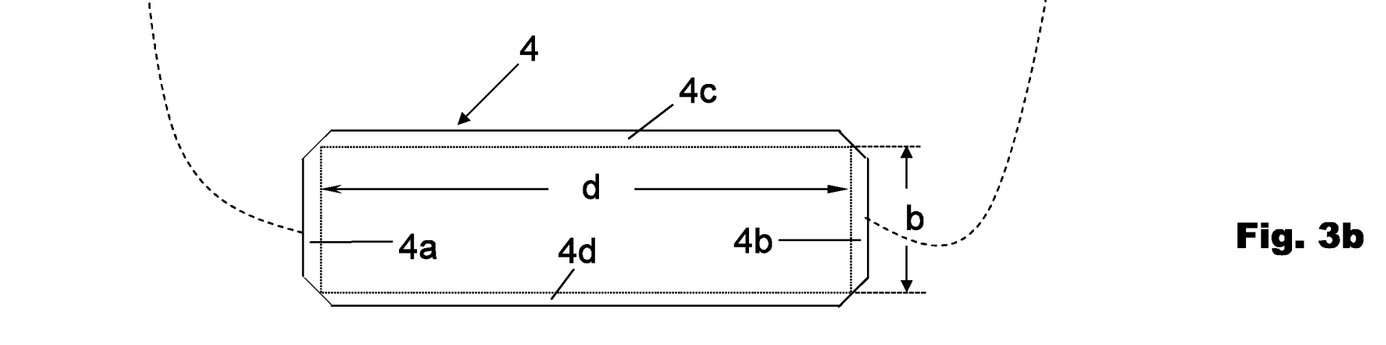
FIG. 3b: A schematic representation of the configuration and manufacture of a tourniquet cuff according to the present disclosure, showing the (unstretched) stretchable wall.

To manufacture a tourniquet cuff 10 according to the present disclosure, an elongated support 3 made of a bendable and air-tight, but unstretchable or only just stretchable support material and extending along a longitudinal direction L and is used. Suitably, the support 3 has the shape of a rectangular strip with two parallel longitudinal edges 3*c*, 3*d* extending in the longitudinal direction L, which edges define a length t of the support, and transverse edges 3*e*, 3*f* disposed perpendicular thereto, which edges define a width b of the support, with the support 3 having an inside surface 3*a* and an outside surface 3*b*. A stretchable wall 4 made of a stretchable material and also having an elongated shape is placed on top of the support 3. To this end, the stretchable wall 4 is suitably also configured in the shape of an elongated strip and cut to size so that its unstretched length d is shorter than the length t of the support, as shown in FIG. 3. The width of the stretchable wall 4 can correspond to the width b of the support or, if a biaxially stretchable material is used, said width can be (slightly) shorter.

Figure 3C:
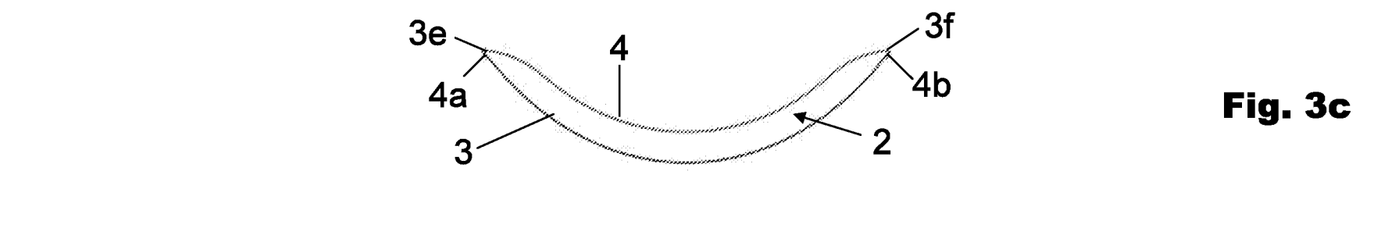
FIG. 3c: A schematic representation of the configuration and manufacture of a tourniquet cuff according to the present disclosure, showing a lateral view of the support and the stretchable wall attached thereon while stretching it.

Suitably, the stretchable wall 4 has edge portions 4*a*, 4*b*, 4*c*, 4*d*, which circumferentially extend both in the longitudinal direction L and in the transverse direction of the wall and which adjoin, respectively, the (unstretched) length d and the width b of the stretchable wall. The stretchable wall 4 is placed on top of the inside surface 3*a* of the support 3 (as indicated by the broken arrows in FIG. 3) and, while the stretchable material is stretched in the longitudinal direction L to the length t of the support, is affixed to the support 3 by gluing or heat-sealing the edge portions 4*a*-4*d* to the support 3. The edge portions 4*a*-4*d* of the stretchable wall 4 are suitably turned down and folded over the support 3 so that they can be glued or heat-sealed to its outside surface 3*b*. When the stretchable wall 4 is attached to the support 3, the stretchable wall 4 is stretched (because the length d of the support is shorter than the length t). Attaching the edge portions 4*a*-4*d* to, and thereby pre-tensioning the stretchable wall 4 on, the support 3 causes the stretchable wall 4 to curve convexly away from the inside surface 3*a* of the support. This is shown in FIG. 3*c*. As a result, an air-tight inflatable chamber 1 is formed between the inside surface 3*a* of the support 3 and the (convexly curved) stretchable wall 4, which chamber extends between the oppositely lying ends 2*a*, 2*b* of the inflatable body 2 formed by the support 3 and the stretchable wall 4. The stretching of the stretchable wall 4 causes the wall to exert a tensile stress on the bendable support 3, which has the effect of circularly deforming the support 3, with the radius of the circular deformation being dependent on the tensile stress which the stretched stretchable wall 4 exerts on the support 3. Suitably, this tensile stress is high enough so that the oppositely lying ends 2*a*, 2*b* of the inflatable body 2 are joined end-to-end or overlap each other. This leads to the formation of a essentially toroidally bent inflatable body 2, wherein the outside surface 3*b* of the support 3, which, due to bending, has an annular shape, is radially on the outside and the stretched stretchable wall 4 is radially on the inside.

To connect the hose 15, which can be, e.g., a compressed air hose, an opening 18 is formed into the inflatable body 2. The opening 18 can be formed during the production of the support 3 as a cut-out or a bore in the support material. The opening 18 is suitably disposed in the area of a longitudinal edge or a transverse edge on one end of the inflatable body 2. A connecting part for a hose 15 or a hose section which can be connected to a compressed gas source is disposed on this opening 18. In a last step, a fastening means, for example, in the form of a fastening tape 17 with a fastener 16 or a Velcro fastening tape is affixed to the outside surface 3*b* of the support 3.

What is claimed is:

1. A tourniquet cuff for placement on a limb, the tourniquet cuff comprising an inflatable body which encloses an inflatable chamber and which is inflatable with compressed gas from an uncompressed state so as to create blood flow restriction in the limb, wherein the inflatable body is formed from an elongated support made of a bendable support material extending along a longitudinal direction and from a stretchable wall made of a stretchable material attached to the support, wherein the stretchable wall is stretched at least in the longitudinal direction even when the inflatable body is not pressurized, wherein the inflatable body comprises two oppositely lying ends and, between said two ends, longitudinal edges extending in the longitudinal direction, wherein the stretchable wall, on both ends and along the longitudinal edges, is air-tightly attached to the support, and wherein the inside diameter of the inflatable body is largest in the area of the two longitudinal edges and smallest in the area of the longitudinal center axis.

2. The tourniquet cuff of claim 1, wherein, when the tourniquet cuff is applied, the inflatable body is bent into the form of a torus, with the support being radially positioned on the outside and with the stretchable wall resting against the limb.

3. The tourniquet cuff of claim 1, wherein the support material is bendable but not elastic.

4. The tourniquet cuff of claim 1, wherein the ratio of the modulus of elasticity of the support material to the modulus of elasticity of the stretchable material is greater than 10.

5. The tourniquet cuff of claim 1, wherein the stretchable wall is convexly curved and, when unpressurized, is at a maximum distance from the support in the area of the longitudinal center axis, which distance is in a range of 1 to 3 cm.

6. The tourniquet cuff of claim 1, wherein the inflatable chamber extends between a first portion and a second portion of the inflatable body, with the first portion being formed by the stretchable wall and the second portion being formed by the support.

7. The tourniquet cuff of claim 1, wherein the stretchable material is selected from the group comprising elastomeric polymers, thermoplastic elastomers (TPE) and terpolymeric elastomers, rubber, ethylene propylene diene monomer (EPDM) rubber and ethylene propylene monomer (EPM) rubber, rubber and silicones, and stretchable woven or knitted fabrics which are coated with a gas-tight and stretchable material.

8. The tourniquet cuff of claim 1, wherein the stretchable material has at least one of the following material properties: a Shore hardness in a range of 17 to 100 Shore A and a modulus of elasticity of 0.05 to 10 MPa.

9. The tourniquet cuff of claim 1, wherein the cross section of the stretchable wall, both when the inflatable body is not pressurized and when it is inflated, is convexly curved.

10. The tourniquet cuff of claim 1, wherein the inflatable body has at least one opening to which a hose can be attached so as to connect the inflatable body to a compressed gas source.

11. The tourniquet cuff of claim 10, wherein the at least one opening is disposed in the area of a longitudinal edge or a transverse edge of the inflatable body.

12. The tourniquet cuff of claim 1, wherein the support is formed from a flat plastic plate or from a metal sheet.

13. The tourniquet cuff of claim 12, wherein the support is formed from a flat plastic which includes a thermoplastic material.

14. The tourniquet cuff of claim 1, wherein, due to the tensile stress exerted by the stretched stretchable wall, the support is bent into an annular shape.

15. The tourniquet cuff of claim 1, wherein, when not pressurized, the inflatable body is dimensionally stable and free of creases.

16. The tourniquet cuff of claim 1, wherein, even when not pressurized, the inflatable body, due to the pre-tensioning of the stretchable wall on the support, is bent into the form of a torus, with the support being radially positioned on the outside and with the two oppositely lying ends of the inflatable body overlapping each other or being joined end-to-end.

17. A method of producing a tourniquet cuff comprising an inflatable body which is formed from an elongated support made of a gas-tight and bendable support material extending in a longitudinal direction and a stretchable wall made of a gas-tight stretchable material and attached to the support, the method comprising:

providing an elongated support with a predefined length extending in a longitudinal direction, providing an elongated stretchable wall with a predefined length extending along a longitudinal direction, with the length of the stretchable wall being shorter than the length of the support and with the stretchable wall comprising circumferential edge portions, attaching the edge portions of the stretchable wall, while the stretchable material is stretched at least in the longitudinal direction, to the elongated support, thereby creating a gas-tight inflatable chamber between the support and the stretchable wall.

18. The method of claim 17, wherein the support material initially has a flat and strip-type shape and comprises an inside surface and an outside surface, with the stretchable wall being attached, while stretching the stretchable wall, to the support so as to be positioned opposite to the inside surface, which causes the support material to be bent into an annular shape and the inside surface to be radially positioned on the inside.

* * * * *